United States Patent
Parker et al.

[11] Patent Number: 5,899,691
[45] Date of Patent: May 4, 1999

[54] JAW EXERCISER/STRENGTHENER

[75] Inventors: Jonathan A. Parker, Plymouth; John S. Tregillis, Coon Rapids, both of Minn.

[73] Assignee: Sentage Corporation, Minneapolis, Minn.

[21] Appl. No.: 08/572,651

[22] Filed: Dec. 14, 1995

[51] Int. Cl.⁶ .................................. A61C 3/00; A61C 5/14
[52] U.S. Cl. .................................. 433/6; 601/38; 128/861
[58] Field of Search .................................. 601/38; 433/6; 128/859, 860, 861, 862

[56] References Cited

U.S. PATENT DOCUMENTS

| | | |
|---|---|---|
| 1,998,203 | 4/1935 | Roemisch . |
| 2,459,273 | 1/1949 | Freedland ................. 128/861 |
| 2,904,791 | 9/1959 | Chandler ................. 128/861 |
| 3,295,519 | 1/1967 | Gerber . |
| 3,454,001 | 7/1969 | Stockfisch ................. 433/6 |
| 3,518,988 | 7/1970 | Gores . |
| 3,532,091 | 10/1970 | Lerman . |
| 3,864,832 | 2/1975 | Carlson ................. 128/862 |
| 3,924,638 | 12/1975 | Mann . |
| 4,185,817 | 1/1980 | Peterson . |
| 4,196,902 | 4/1980 | Borriello . |
| 4,799,500 | 1/1989 | Newbury . |
| 5,406,963 | 4/1995 | Adell . |

*Primary Examiner*—Nicholas D. Lucchesi
*Attorney, Agent, or Firm*—Hugh D. Jaeger

[57] ABSTRACT

One-piece jaw exerciser/strengthener, custom fit, aligned and located over and about the teeth of the upper or lower jaw including one or more resilient substantially tubular members on an exterior surface, which resiliently interface with teeth of the upper or lower jaw. The jaw exerciser/strengthener can be custom formed over a dental casting, or can be formed by heating of the device and biting down to cause a conformed fit to the upper or lower jaw teeth and/or gum area.

2 Claims, 10 Drawing Sheets

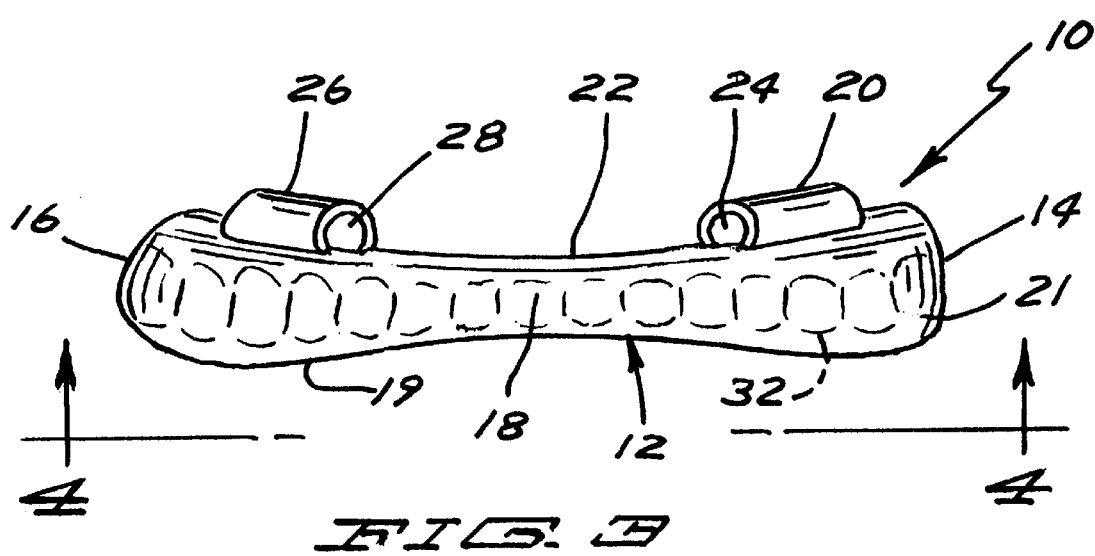

JAW EXERCISER/STRENGTHENER

BACKGROUND OF THE INVENTION

1. Field of the Invention

The present invention is for a dental device, and more particularly, pertains to a therapeutic jaw exerciser/strengthener.

2. Description of the Prior Art

One prior art construction used for this function was sections of rubber tubing (surgical tubing which was cut into small pieces). The patient would place the tubing over the back teeth and was instructed to chew gently according to a specific protocol/program. However, the tubing was not held onto the teeth, so it would move around in the mouth while the patient was attempting to chew or bite on the tubing. This was extremely frustrating for the patient and was not very effective.

It is also known that when a joint is painful or is not functioning properly, there is a reflex inhibition of the muscles which support that joint to avoid injury and increase pain. In order to rehabilitate these muscles and joints in patients experiencing difficulty with jaw function or jaw pain, a device is necessary to promote increasing function.

The present invention helps to accomplish that task. Therefore, patients are placed on a specific exercise program which will include the use of the invention in addition to other aspects of the protocol (appropriate stretching/mobilization techniques, massage techniques, softer diet, hot packs, etc.).

SUMMARY OF THE INVENTION

The general purpose of the present invention is to provide an exerciser/strengthener device which is made of any flexible material: for example a thermoplastic material such as polyvinyl, ethylvinyl acetate, or other comparable acrylic or vinyl material. This device fits over all or part of the mandibular teeth or maxillary teeth. The device may cover some of the posterior teeth, unilaterally or bilaterally, or a few or all of the anterior teeth. The appliance is customized to fit over the teeth and a custom fit holds the device in place. The device includes a built-in resilient substantially tubular member which can vary in shape (circular, rectangular, square, etc.). This member, which is an integral part of the device, can be sealed and lined or filled with a resilient and somewhat compression resistant object, or resilient filling material, such as silicone, which will allow resistance to function of the joint and muscles when the opposing teeth come in contact with this member. Therefore, the patient can close or bite gently on the member and the member will remain in a stable position to resist the forces of biting and exercise the muscles and allow joint function.

The device is used to strengthen and reduce fatigue in the jaw muscles for patients experiencing these symptoms. It can also be used in patients who have pain in the temporomandibular joint (TMJ) during jaw function. The device can be used by surgeons after jaw surgery to rehabilitate jaw function after a patient has had a fracture or a surgical procedure to treat a malocclusion. These patients generally are not able to or allowed to use their jaws for a 4–6 week period following the fracture or surgery. In order to rehabilitate jaw function, this device can be used to strengthen the muscles and improve temporomandibular joint (TMJ) function after an extended period of disuse.

The invention can include customized laboratory fabrication (indirect method on a dental cast), or fabrication of a one-size-fits-all type of device most likely made of a polymer, polyvinyl, ethylvinyl acetate or other resilient boil and bite material.

According to one embodiment of the present invention, there is provided a one-piece jaw exerciser/strengthener, including a main body formed over and about the lower jaw teeth, inner and outer vertical main body walls, an interior surface which conforms to the shape of the lower jaw teeth, and opposing resilient substantially tubular members located along and about the upper surface of the main body.

According to a first alternative embodiment of the present invention, there is provided a one-piece jaw exerciser/strengthener having a forwardly and centrally located resilient substantially tubular member in addition to substantially tubular members located at the sides.

According to a second alternative embodiment of the present invention, there is provided a two-piece jaw exerciser/strengthener.

According to a third alternative embodiment of the present invention, there is provided a jaw exerciser/strengthener having only a centrally located resilient substantially tubular member.

According to a fourth alternative embodiment of the present invention, there is provided a jaw exerciser/strengthener having resilient substantially tubular member having generally trapezoidal cross sections.

One significant aspect and feature of the present invention is a one-piece jaw exerciser/strengthener.

Another significant aspect and feature of the present invention is a jaw exerciser/strengthener which fits and aligns over and about the teeth of the lower or upper jaw.

Yet another significant aspect and feature of the present invention is a jaw exerciser/strengthener which exhibits stability for exercise or strengthener use, therefore providing stability for the temporomandibular joint (TMJ).

Still another significant aspect and feature of the present invention is the utilization of one or more resilient substantially tubular members integral to a main body.

A further significant aspect and feature of the present invention is an indirect method in which the device is custom fit over and about a dental cast which is a replica of the patient's dental arch (teeth).

A still further significant aspect and feature of the present invention is a direct custom fit whereby the device is heated to provide a formable member which is shaped to the contour of the teeth as the patient exerts force by biting down on the interceding member.

Another significant aspect and feature of the present invention is a jaw exerciser/strengthener having resilient substantially tubular members located at the sides of a main body.

Another significant aspect and feature of the present invention is a jaw exerciser/strengthener having a resilient substantially tubular member located at the front and center of a main body.

Another significant aspect and feature of the present invention is a jaw exerciser/strengthener having a left body member half and a right body member half.

Having thus described embodiments of the present invention, it is the principal object of the present invention to provide a jaw exerciser/strengthener.

One object of the present invention is a jaw exerciser/strengthener for therapeutic rehabilitation of the jaws.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 3 illustrates a front view of the jaw exerciser/strengthener;

DETAILED DESCRIPTION OF THE PREFERRED EMBODIMENTS

Figure 1:
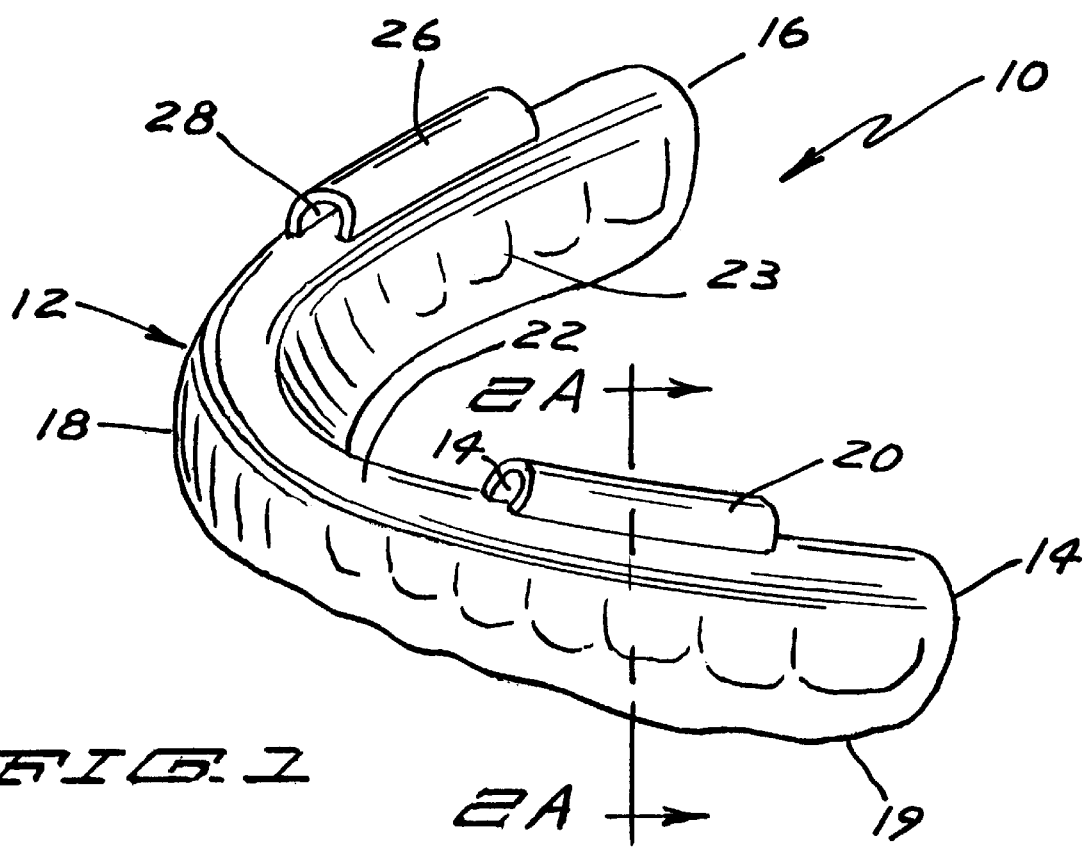
FIG. 1 illustrates a perspective view of a jaw exerciser/strengthener having two side resilient substantially tubular members.

FIG. 1 illustrates a perspective view of a jaw exerciser/strengthener 10, the present invention. The one-piece jaw exerciser/strengthener 10 is formed of a resilient thermoplastic material such as, but not limited to, polyvinyl, ethylvinyl acetate, or other such suitable comparable acrylic or vinyl material. The jaw exerciser/strengthener 10 includes a one-piece main body 12 conforming to the shape of all or part of the mandibular or maxillary teeth. The one-piece main body 12, which is substantially U-shaped, includes a left end 14, a right end 16, and a center portion 18 aligned therebetween. An outer substantially vertical wall 21 and an inner substantially vertical wall 23 extend between the left and right ends 14 and 16. A continuous rounded edge 19, which is comfortable to the mouth, extends along the lower surface of the main body 12. An integral resilient substantially tubular member 20, having beveled ends, is located at the upper exterior rounded surface 22 between the center portion 18 and the left end 14. An interior space 24 which is hollow can be lined with a resilient and somewhat compression resistant object or filling material to provide for varying degrees of resiliency of the resilient substantially tubular member 20. A like resilient substantially tubular member 26 having a hollow interior space 28 opposes the resilient substantially tubular member 20 on the upper exterior rounded surface 22 between the center portion 18 and the right end 16. Although resilient substantially tubular members 20 and 26 are illustrated as being generally round in cross section, any other suitable predetermined geometrical configuration or shape, such as square, rectangular, semi-circular, or the like can be utilized. In the alternative, the resilient substantially tubular members 20 and 26 can be sealed on each end for accommodation of air, inert gas, liquids, or resilient material, such as silicone, filling or partially filling the sealed resilient substantially tubular members 20 and 26.

Figure 2A:
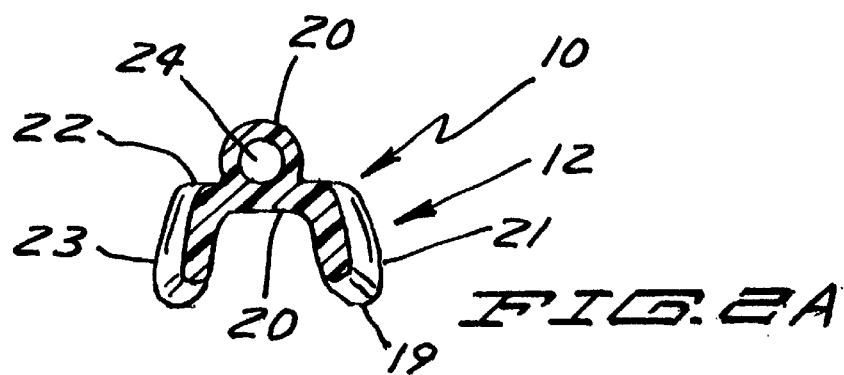
FIG. 2A illustrates a cross sectional view of the jaw exerciser/strengthener along line 2A—2A of FIG. 1.

FIG. 2A illustrates a cross sectional view of the jaw exerciser/strengthener 10 along line 2A—2A of FIG. 1, where all numerals correspond to those elements previously described. The jaw exerciser/strengthener 10 includes an interior inverted substantially U-shaped surface 30 which conforms to the shape of the teeth of the lower jaw. The conforming fit can be achieved in a dental laboratory over a dental cast which is a replica of the patient's lower teeth or by a boil and bite method whereby the device, constructed of a suitable heat sensitive material, is boiled or otherwise heated.

Figure 2B:
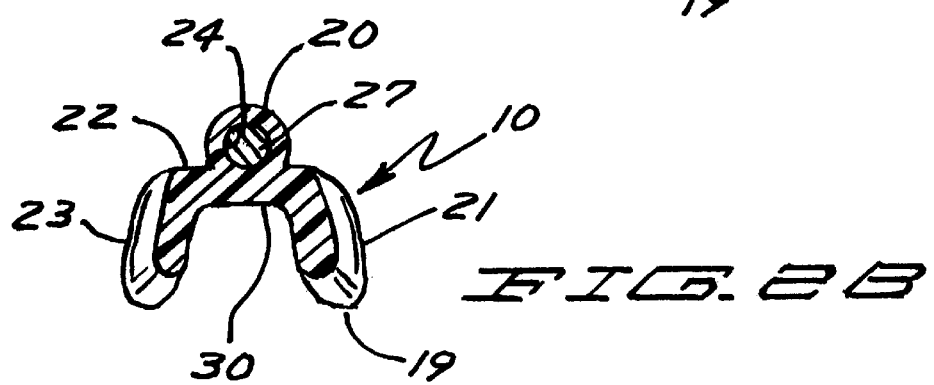
FIG. 2B illustrates a cross sectional view of the jaw exerciser/strengthener as in the view of FIG. 2A, but including a cylindrical rod.

FIG. 2B illustrates a cross sectional view of the jaw exerciser/strengthener 10 as in the view of FIG. 2A but including a cylindrical rod 27 or otherwise suitably shaped member, where all numerals correspond to those elements previously described. The cylindrical rod 27 is held by friction within the resilient substantially tubular members 20 and 26 on the upper exterior surface of the jaw exerciser/strengthener. This rod 27 maintains the integrity of the resilient substantially tubular member 20 and/or 26 during the heating process and acts as a handle. The patient heats the device and places it over the teeth. The patient then bites down on the heated device to cause the material to conform to the patient's teeth for a custom fit. Once the jaw exerciser/strengthener has cooled, the cylindrical rod 27 is removed.

FIG. 3 illustrates a front view of the jaw exerciser/strengthener 10, where all numerals correspond to those elements previously described. It is noted that teeth impressions 32 along the interior surface (shown in dashed lines) are illustrated as formed during the forming process.

Figure 4:
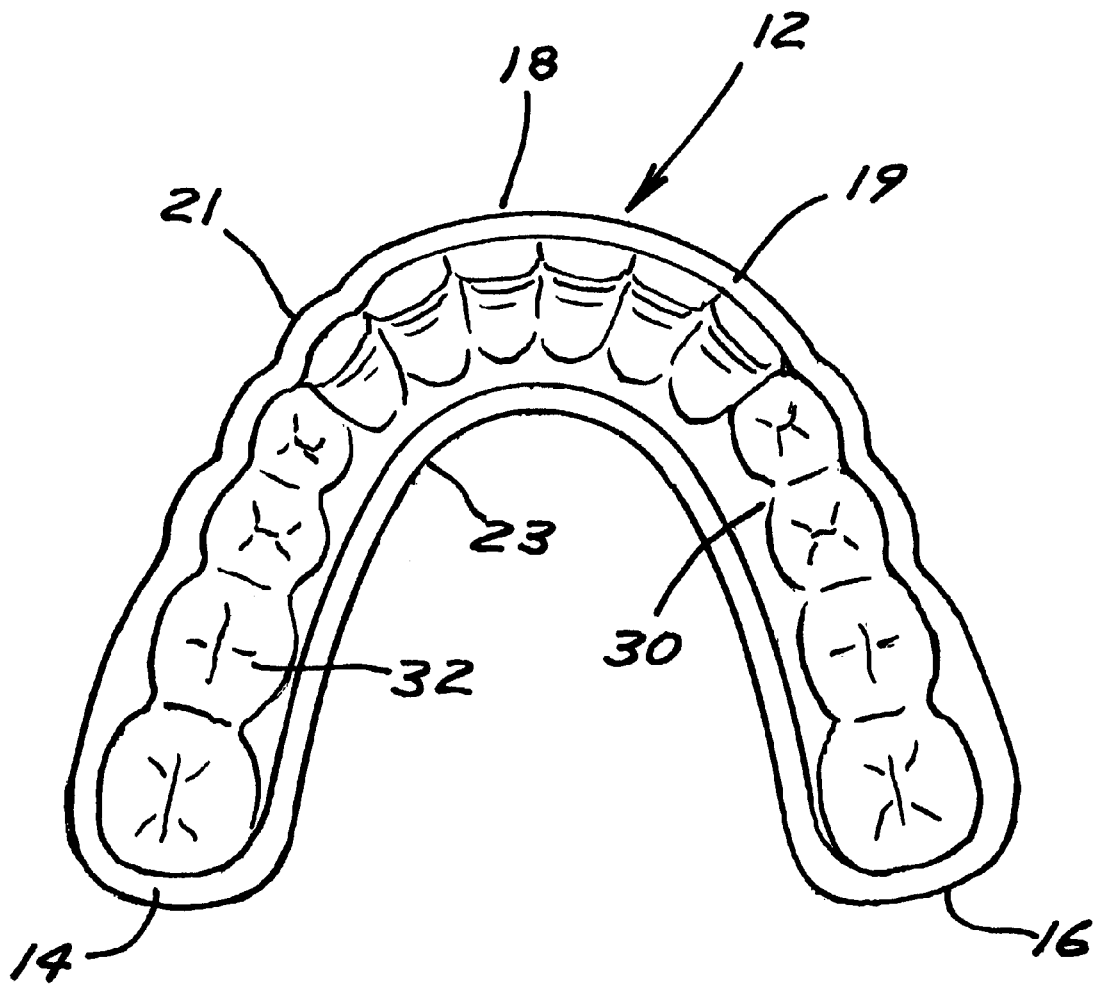
FIG. 4 illustrates a bottom view of the jaw exerciser/strengthener along line 4—4 of FIG. 3.

FIG. 4 illustrates a bottom view of the jaw exerciser/strengthener 10 along line 4—4 of FIG. 3, where all numerals correspond to those elements previously described. Illustrated in particular are the teeth impressions 32 which are custom formed along the interior surface 30, as previously described.

Figure 5:
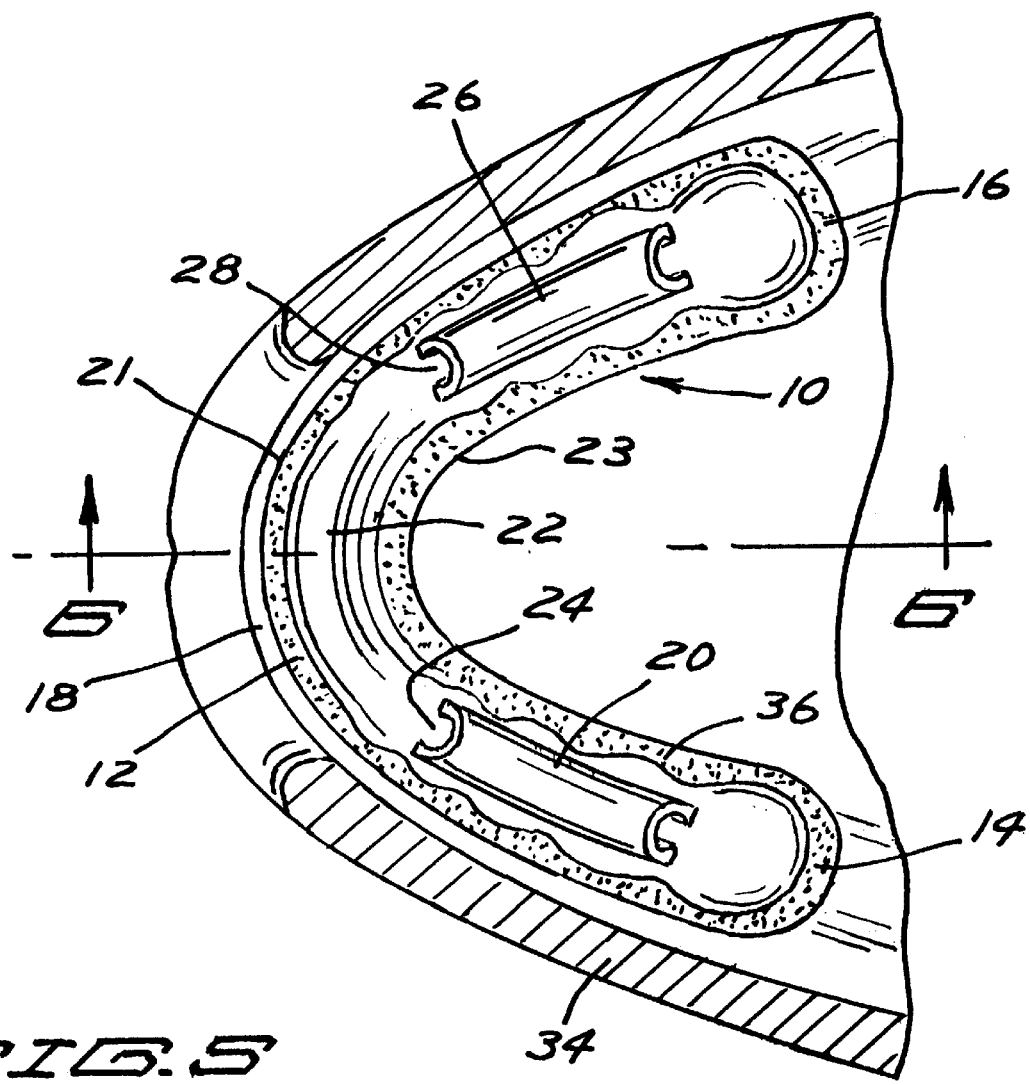
FIG. 5 illustrates a top view of the jaw exerciser/strengthener applied over the lower teeth.

FIG. 5 illustrates a top view of the jaw exerciser/strengthener 10 applied over the teeth 36 of the lower jaw 34, where all numerals correspond to those elements previously described.

Figure 6:
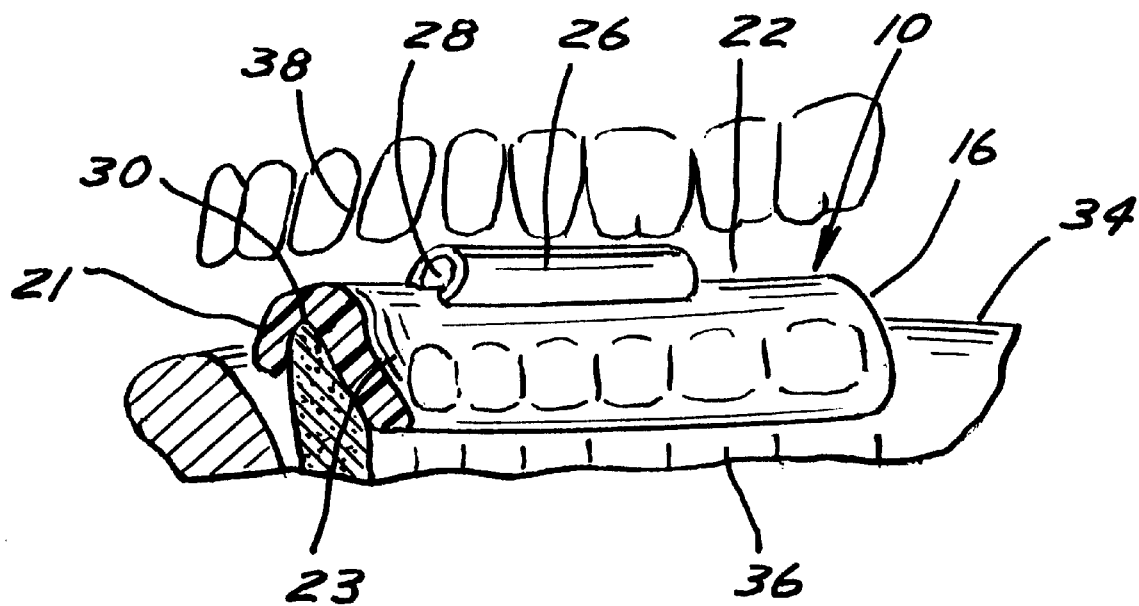
FIG. 6 illustrates a cross sectional view of the jaw exerciser/strengthener applied over the lower teeth along line 6—6 of FIG. 5.

FIG. 6 illustrates a cross sectional view of the jaw exerciser/strengthener 10 applied over the teeth 36 of the lower jaw 34 along line 6—6 of FIG. 5, where all numerals correspond to those elements previously described. A set of upper teeth 38 are illustrated in engagement with the resilient substantially tubular member 26 for purposes of exercising or strengthening.

FABRICATION TECHNIQUES

The device can be fabricated by a dental laboratory, and customized to fit over a dental cast which is a replica of the patient's upper or lower teeth. Alternatively, a one-size-fits-all "boil and bite" type appliance can be distributed directly without customized fabrication at a dental laboratory. The boil and bite technique is completed by the patient under the direction/supervision of a health care provider after the device has been purchased, and then is customized and fabricated directly in the mouth by the patient. The device can be made available from dentists and dental specialists, physical therapists, and other health care providers who deal with jaw problems.

ALTERNATIVE EMBODIMENTS

Figure 7:
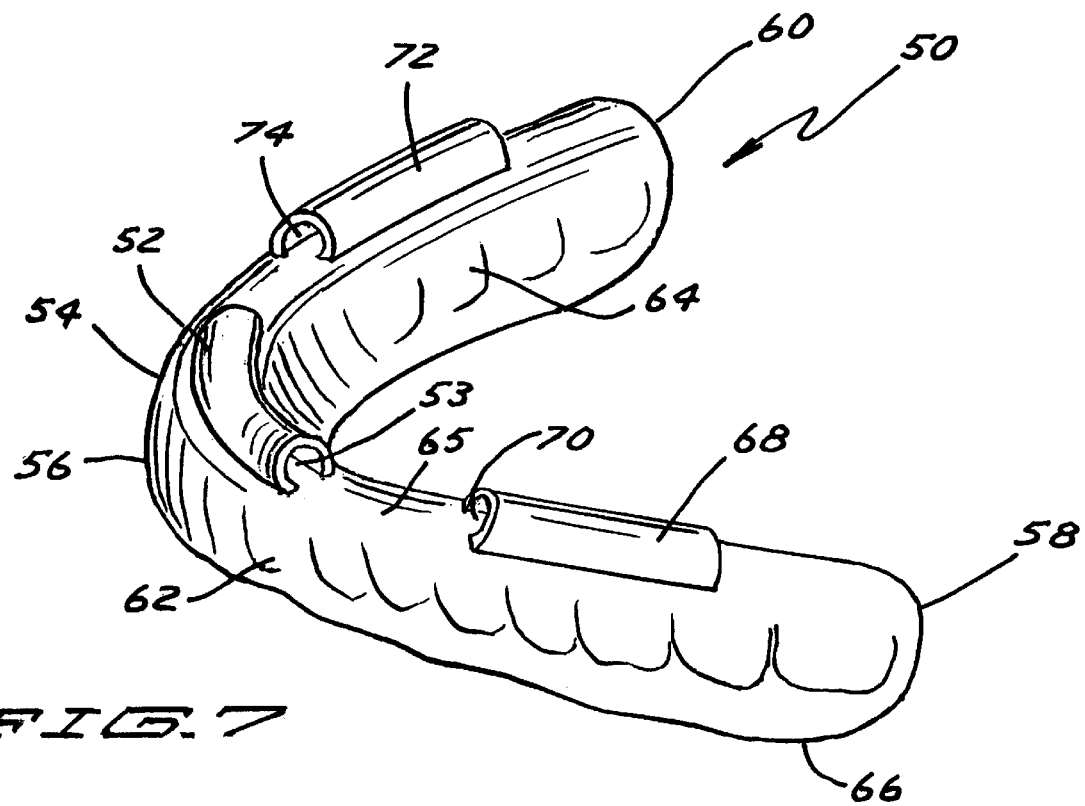
FIG. 7, a first alternative embodiment, illustrates a perspective view of a jaw exerciser/strengthener having a centrally located resilient substantially tubular member in addition to the two side resilient substantially tubular members.

FIG. 7, a first alternative embodiment, illustrates a one-piece jaw exerciser/strengthener 50 similar in design and construction to the jaw exerciser/strengthener 10 of FIG. 1, but which includes an additional resilient substantially tubular member 52 having a hollow interior space 53 aligned to and conforming to the shape of a center portion 54 of the substantially U-shaped main body 56. The jaw exerciser/strengthener 50 also includes a left end 58, a right end 60, an outer vertical wall 62, an inner vertical wall 64, an upper exterior rounded surface 65, a continuous rounded edge 66, a resilient hollow bevel-ended substantially tubular member 68 between center portion 54 and left end 58 having a hollow interior space 70, and a resilient bevel-ended substantially tubular member 72 between center portion 54 and right end 60 having a hollow interior space 74.

Figure 8:
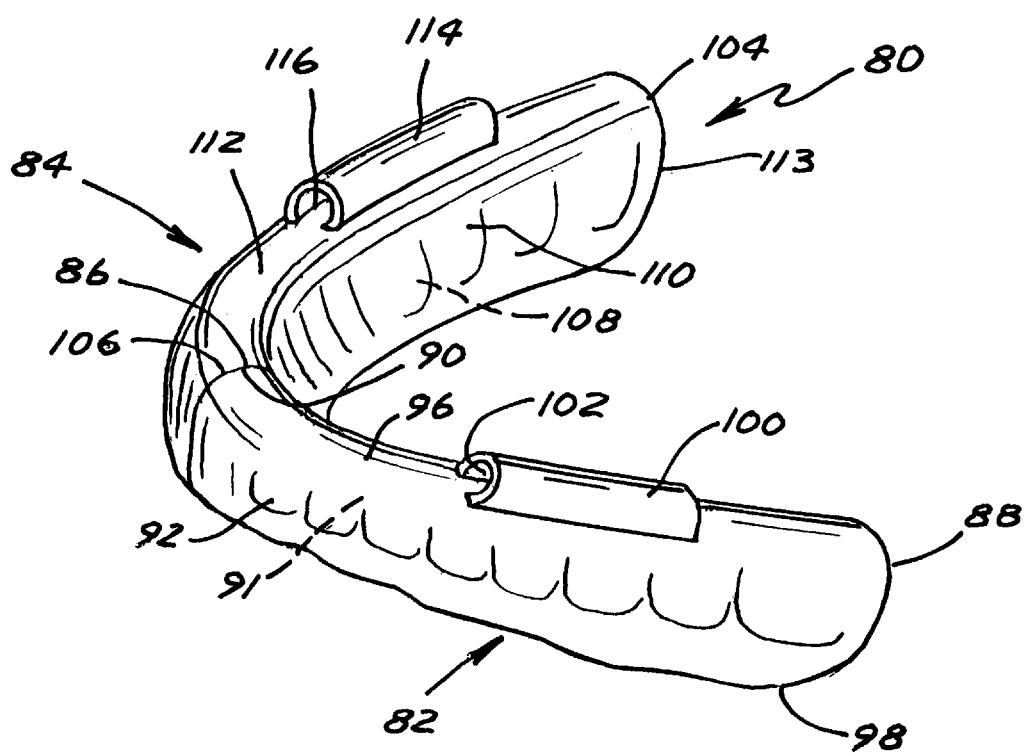
FIG. 8, a second alternative embodiment, illustrates a perspective view of a jaw exerciser/strengthener formed in two halves.

FIG. 8, a second alternative embodiment, illustrates a two-piece jaw exerciser/strengthener 80 similar in design and construction to the jaw exerciser/strengthener 10 of FIG. 1, but which features a substantially U-shaped main body divided into a left body member half 82 and a right body member half 84 which align at juncture 86. Exercising and/or strengthening of either the left jaw or the right jaw can be accomplished using just the left body member half 82 or just the right body member half 84, respectively. Exercising and/or strengthening of both the left and right jaws simultaneously can be accomplished by use of both left and right body member halves 82 and 84. The left body member half 82 includes a left end 88, a right end 90 which mates to a corresponding end of the right body member half 84 at juncture 86, an outer vertical wall 92, an inner vertical wall 94 opposing outer vertical wall 92, an upper exterior rounded surface 96, a continuous rounded edge 98, and a resilient bevel-ended substantially tubular member 100 between the right end 90 and the left end 88 having a hollow interior space 102.

The left body member half 84 includes a right end 104, a left end 106 which mates to a corresponding end 90 of the left body member half 82 at juncture 86, an outer vertical wall 108, an inner vertical wall 110 opposing outer vertical wall 108, an upper exterior rounded surface 112, a continuous rounded edge 113, and a resilient bevel-ended substantially tubular member 114 between the left end 106 and the right end 104 having a hollow interior space 116.

Figure 9:
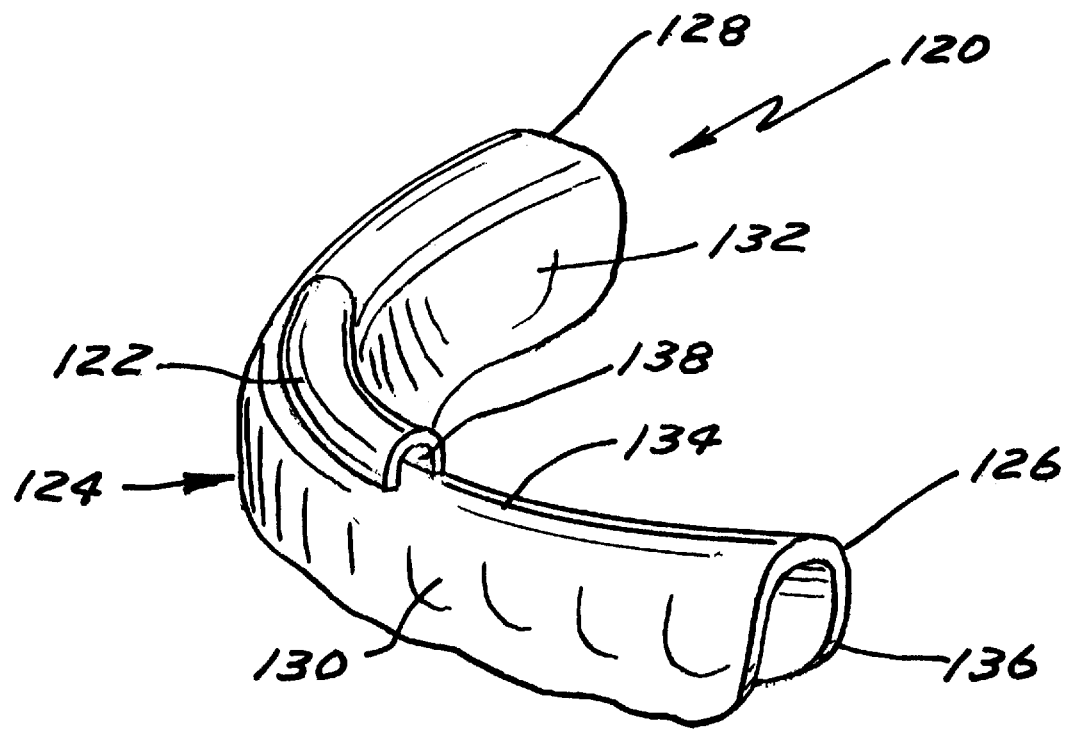
FIG. 9, a third alternative embodiment, illustrates a perspective view of a jaw exerciser/strengthener having only a centrally located resilient substantially tubular member; and, FIG. 10, a fourth alternative embodiment, illustrates a perspective view of a jaw exerciser/strengthener having resilient substantially tubular member having generally trapezoidal cross sections.

FIG. 9, a third alternative embodiment, illustrates a one-piece jaw exerciser/strengthener 120 incorporating a single centrally located resilient substantially tubular member 122 similar to the resilient substantially tubular member 52 described with respect to FIG. 7. The centrally located resilient substantially tubular member 122 is used for contacting incisors at the dental arch apex and extends along and conforms to the slight curvature of the central portion of a substantially U-shaped main body 124 which is a shortened version of the substantially U-shaped main body 56 of FIG. 7. The substantially U-shaped main body 124 includes a left end 126, a right end 128, an outer vertical wall 130, an inner vertical wall 132 opposing the outer vertical wall 130, an upper exterior rounded surface 134 along which the resilient substantially tubular member 122 aligns, and a continuous rounded edge 136. The bevel-ended resilient substantially tubular member 122 includes a hollow interior space 138.

Figure 10:
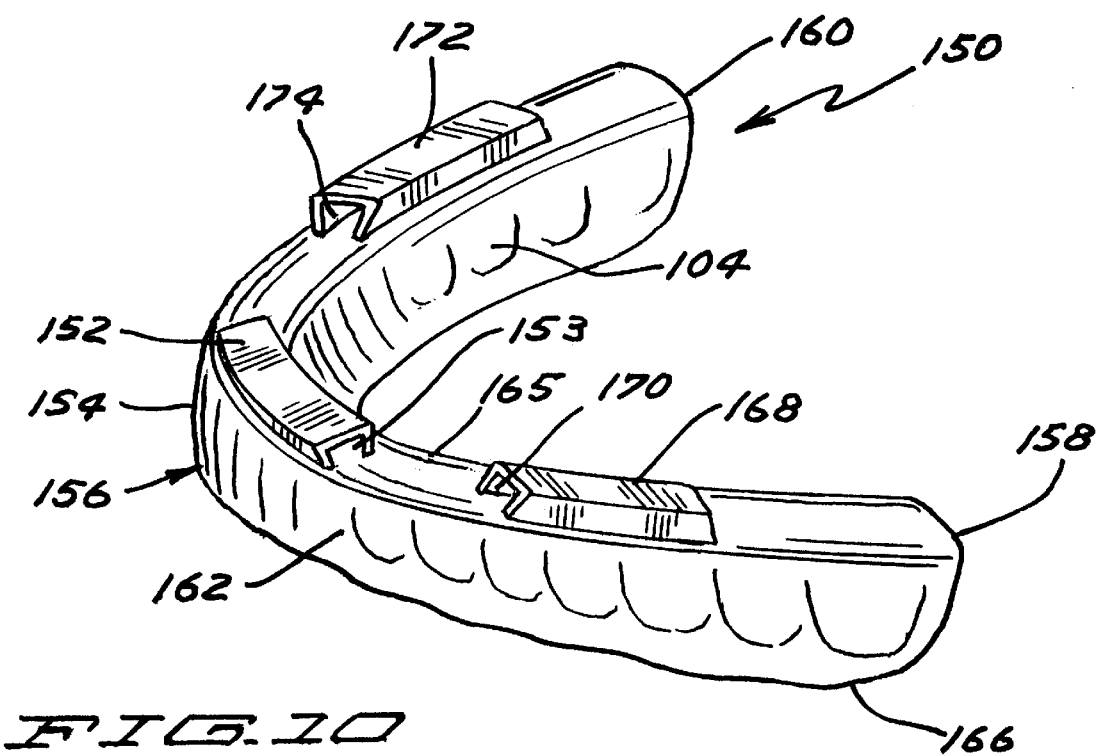

FIG. 10, a fourth alternative embodiment, illustrates a one-piece jaw exerciser/strengthener 150 featuring resilient substantially tubular members having a generally trapezoidal cross section in lieu of a generally round cross section and is similar, in most respects, in design and construction to the jaw exerciser/strengthener 10 of FIG. 1, as well as the other described embodiments. The jaw exerciser/strengthener 150 includes a resilient substantially tubular member 152 having a generally trapezoidal cross section and a generally trapezoidal hollow interior space 153 aligned to and conforming to the shape of a center portion 154 of the substantially U-shaped main body 156. The jaw exerciser/strengthener 150 also includes a left end 158, a right end 160, an outer vertical wall 162, an inner vertical wall 164, an upper exterior rounded surface 165, a continuous rounded edge 166, a resilient bevel-ended substantially tubular member 168 between center portion 154 and left end 158 having a generally trapezoidal cross section and a generally trapezoidal hollow interior space 170, and a resilient bevel-ended substantially tubular member 172 between center portion 154 and right end 160 having a generally trapezoidal cross section and a generally trapezoidal hollow interior space 174.

Various modifications can be made to the present invention without departing from the apparent scope hereof.

We claim:

1. In a device adapted to be inserted into the mouth of a user in close proximity to the teeth of the user for the exercise of muscles associated with the jaws, the improvement comprising:

a. a substantially U-shaped main body member of polymeric material;

b. said substantially U-shaped main body member having an interior surface generally conforming to the shape of the lower or the upper teeth of the user;

c. said substantially U-shaped main body member having an exterior rounded surface;

d. at least one resilient substantially tubular member affixed to said exterior rounded surface;

e. said at least one resilient substantially tubular member being positioned to engage the upper teeth of said user when said substantially U-shaped main body member is positioned over the lower teeth of the user and the upper and lower jaws are moved toward each other, whereby the jaw muscles of the user are exercised against the resistance provided by said at least one resilient substantially tubular member;

f. said interior surface of said substantially U-shaped main body member of polymeric material is shaped to conform to a dental cast of the lower teeth of the user; and, g. said at least one resilient substantially tubular member has a generally trapezoidal cross section.

2. In a device adapted to be inserted into the mouth of a user in close proximity to the teeth of the user for the exercise of muscles associated with the jaws, the improvement comprising:

a. a substantially U-shaped main body member of polymeric material;

be said substantially U-shaped main body member having an interior surface generally conforming to the shape of the lower or the upper teeth of the user;

c. said substantially U-shaped main body member having an exterior rounded surface;

d. at least one resilient substantially tubular member affixed to said exterior rounded surface;

e. said at least one resilient substantially tubular member being positioned to engage the upper teeth of said user when said substantially U-shaped main body member is positioned over the lower teeth of the user and the upper and lower jaws are moved toward each other, whereby the jaw muscles of the user are exercised against the resistance provided by said at least one resilient substantially tubular member;

f. said interior surface of said substantially U-shaped main body member of polymeric material is adapted to be shaped to conform to the lower or upper teeth of the user by heating and insertion into the user's mouth while still warm for form-fitting to the lower or upper teeth of the user; and, g. said at least one resilient substantially tubular member has a generally trapezoidal cross section.

* * * * *